(12) United States Patent
Tseng et al.

(10) Patent No.: US 12,179,171 B2
(45) Date of Patent: Dec. 31, 2024

(54) PYRAZOLE METAL COMPLEX FOR ABSORBING CARBON DIOXIDE, METHOD FOR PREPARING PYRAZOLE METAL COMPLEX, AND METHOD FOR ABSORPTION OF CARBON DIOXIDE

(71) Applicant: National Tsing Hua University, Hsinchu (TW)

(72) Inventors: Yu-Ting Tseng, Hsinchu (TW); Tsai-Te Lu, Hsinchu (TW); Tsu-Chieh Yu, Hsinchu (TW); Wen-Feng Liaw, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 18/299,669

(22) Filed: Apr. 12, 2023

(65) Prior Publication Data

US 2023/0241579 A1 Aug. 3, 2023

Related U.S. Application Data

(62) Division of application No. 17/550,382, filed on Dec. 14, 2021, now abandoned.

(Continued)

(30) Foreign Application Priority Data

Jul. 28, 2021 (TW) .................. 110127682

(51) Int. Cl.
| | | |
|---|---|---|
| *C07F 1/04* | (2006.01) | |
| *B01D 53/62* | (2006.01) | |
| *B01D 53/81* | (2006.01) | |
| *B01J 20/22* | (2006.01) | |
| *C07F 1/00* | (2006.01) | |

(Continued)

(52) U.S. Cl.
CPC ............ *B01J 20/223* (2013.01); *B01D 53/62* (2013.01); *B01D 53/81* (2013.01); *C07F 1/005* (2013.01); *C07F 1/04* (2013.01); *C07F 1/08* (2013.01); *C07F 3/06* (2013.01); *C07F 13/005* (2013.01); *C07F 15/025* (2013.01);
(Continued)

(58) Field of Classification Search
None
See application file for complete search history.

(56) References Cited

U.S. PATENT DOCUMENTS

2014/0294709 A1    10/2014   Long et al.

FOREIGN PATENT DOCUMENTS

| CN | 102126968 A | 7/2011 |
|---|---|---|
| CN | 102827037 A | 12/2012 |
| CN | 104958996 A | 10/2015 |

OTHER PUBLICATIONS

Yu-Ting Tseng et al. "Dinitrosyl Iron Complex [K-18-crown-6-ether][(NO)2Fe(MePyrCO2)]: Intermediate for Capture and Reduction of Carbon Dioxide"; Angew. Chem. Int. Ed. 2020, 59, pp. 11819-11823.

(Continued)

*Primary Examiner* — Yun Qian
(74) *Attorney, Agent, or Firm* — Muncy, Geissler, Olds & Lowe, P.C.

(57) ABSTRACT

A pyrazole metal complex for absorption of carbon dioxide, a method for preparing the pyrazole metal complex, and a method for absorbing carbon dioxide are provided; wherein the product produced by reacting pyrazole metal complex and carbon dioxide may be transformed into several economically valuable compounds.

8 Claims, 25 Drawing Sheets

Related U.S. Application Data

(60) Provisional application No. 63/173,723, filed on Apr. 12, 2021.

(51) Int. Cl.
*C07F 1/08* (2006.01)
*C07F 3/06* (2006.01)
*C07F 13/00* (2006.01)
*C07F 15/02* (2006.01)
*C07F 15/04* (2006.01)
*C07F 15/06* (2006.01)

(52) U.S. Cl.
CPC .......... *C07F 15/045* (2013.01); *C07F 15/065* (2013.01); *B01D 2253/204* (2013.01); *B01D 2257/504* (2013.01)

(56) References Cited

OTHER PUBLICATIONS

CN104958996 A, English Translation (Year 2015).

PYRAZOLE METAL COMPLEX FOR ABSORBING CARBON DIOXIDE, METHOD FOR PREPARING PYRAZOLE METAL COMPLEX, AND METHOD FOR ABSORPTION OF CARBON DIOXIDE

CROSS REFERENCE TO RELATED APPLICATION

This application is a Divisional of co-pending application Ser. No. 17/550,382 filed on Dec. 14, 2021; and this application claims the benefit of U.S. Provisional Application Ser. No. 63/173,723, filed on Apr. 12, 2021, and the benefit of Taiwan Patent Application Serial No. 110127682 filed on Jul. 28, 2021. The entirety contents of all of which are hereby incorporated by reference.

BACKGROUND OF THE INVENTION

1. Field of the Invention

The present invention relates to a pyrazole metal complex for absorbing carbon dioxide, a method for preparing pyrazole metal complex, and method for absorption of carbon dioxide; particularly, to a pyrazole metal complex for absorbing carbon dioxide in the air, a method for preparing pyrazole metal complex, and method for absorption of carbon dioxide in the air.

2. Description of Related Art

Since the industrial revolution, excessive use of petroleum fuels has caused massive emission of carbon dioxide, which has severely affected the world by causing problems such as the greenhouse effect, seawater acidification, ecological imbalance, and melting icebergs. Accordingly, how to reduce the content of carbon dioxide in the atmosphere and reduce carbon dioxide emissions is an important global issue.

Most of the carbon dioxide capture techniques currently applied in the industry are disadvantageous of oxide sensitive, water sensitive, high volatility, and high demand for renewable energy. Or, the products yield after capturing carbon dioxide are not reusable for synthesizing economically valuable compounds, and can only be stored in the saltwater layer deep underground.

Accordingly, it is desirable to provide a novel carbon dioxide capture technique, which is not sensitive to oxygen or water and the products yielded from capturing carbon dioxide can be converted into other economically valuable compounds. It is also desirable that the compound used for capturing carbon dioxide can be recovered as the original compound and continues to be used to capture carbon dioxide. In this way, the cost of storing the product yield by capturing carbon dioxide can be reduced, and other economically valuable compounds can be synthesized, the compound used to capture carbon dioxide can be reused, and the demand for environmental protection can be met.

SUMMARY OF THE INVENTION

The present invention provides a pyrazole metal complex for absorbing carbon dioxide, wherein the pyrazole metal complex has the structure:

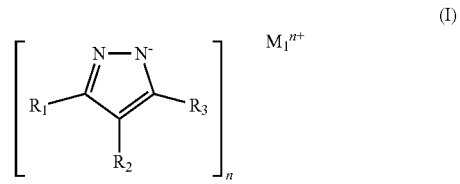

Wherein each of $R_1$, $R_2$, and $R_3$ is independently selected from a group consisting of hydrogen, substituted or unsubstituted $C_1$-$C_6$ alkyl group, and substituted or unsubstituted aryl group; and $M_1^{n+}$ is selected from a group consisting of $Na^+$, $K^+$, $[K\text{-}18\text{-crown-}6\text{ ether}]^+$, $Mn^{2+}$, $Fe^{2+}$, $Fe^{3+}$, $Co^{2+}$, $Co^{3+}$, $Ni^{2+}$, $Cu^{2+}$, $Cu^+$, and $Zn^{2+}$.

In one embodiment, $R_1$ is selected from a group consisting of hydrogen, methyl group, and benzyl group; each of $R_2$ and $R_3$ is independently hydrogen.

In one embodiment, $M_1^{n+}$ is selected from a group consisting of $Na^+$, $K^+$, and $[K\text{-}18\text{-crown-}6\text{ ether}]^+$.

The present invention also provides a preparing method of the abovementioned pyrazole metal complex, which comprises: step (a): providing a pyrazole compound having the structure:

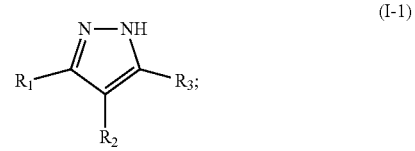

and step (b): reacting a metal hydride with the pyrazole compound of formula (I-1) to obtain the pyrazole metal complex.

In one embodiment, step (b) further comprises tetrahydrofuran as a solvent.

The present invention further provides a method for absorbing carbon dioxide in the air, comprising: step (1): providing a pyrazole metal complex of formula (I):

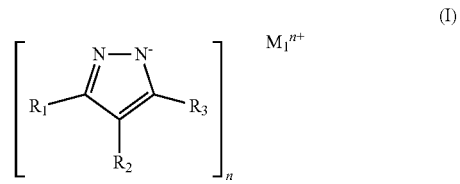

wherein each of $R_1$, $R_2$, and $R_3$ is independently selected from a group consisting of hydrogen, substituted or unsubstituted $C_1$-$C_6$ alkyl group, and substituted or unsubstituted aryl group; and $M_1^{n+}$ is selected from a group consisting of $Na^+$, $K^+$, $[K\text{-}18\text{-crown-}6\text{ ether}]^+$, $Mn^{2+}$, $Fe^{2+}$, $Fe^{3+}$, $Co^{2+}$, $Co^{3+}$, $Ni^{2+}$, $Cu^{2+}$, $Cu^+$, and $Zn^{2+}$; and step (2): reacting the pyrazole metal complex with carbon dioxide for absorbing carbon dioxide, wherein a product obtained by reacting the pyrazole metal complex and carbon dioxide is a pyrazole amide formate of formula (II):

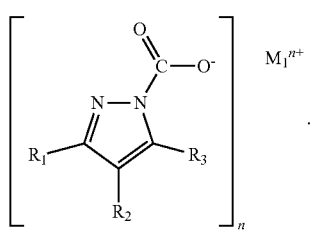
(II)

In one embodiment, $R_1$ is selected from a group consisting of hydrogen, methyl group, and benzyl group; each of $R_2$ and $R_3$ is independently hydrogen.

In one embodiment, $M_1^{n+}$ is selected from a group consisting of $Na^+$, $K^+$, and $[K\text{-}18\text{-crown-}6\ ether]^+$.

In one embodiment, the reaction of the pyrazole metal complex and carbon dioxide is carried out under an inert gas environment in step (2).

The present invention further provides another method for absorbing carbon dioxide, which comprises: step (i): providing a pyrazole metal complex of formula (I)

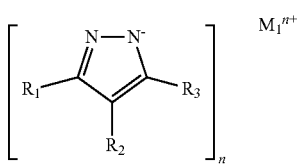
(I)

wherein each of $R_1$, $R_2$, and $R_3$ is independently selected from a group consisting of hydrogen, substituted or unsubstituted $C_1$-$C_6$ alkyl group, and substituted or unsubstituted aryl group; and $M_1^{n+}$ is selected from a group consisting of $Na^+$, $K^+$, $[K\text{-}18\text{-crown-}6\ ether]^+$, $Mn^{2+}$, $Fe^{2+}$, $Fe^{3+}$, $Co^{2+}$, $Co^{3+}$, $Ni^{2+}$, $Cu^{2+}$, $Cu^+$, and $Zn^{2+}$; and step (ii): reacting the pyrazole metal complex with carbon dioxide for absorbing carbon dioxide, wherein a product obtained by reacting the pyrazole metal complex and carbon dioxide is a pyrazole amide formate of formula (II):

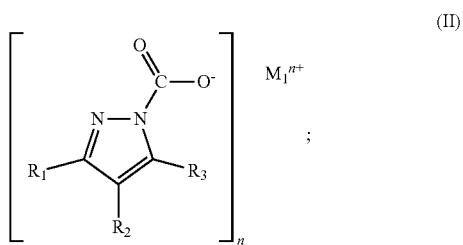
(II)

;

and step (iii): providing a double nitroso iron complex of formula (III) for reacting with the pyrazole amide formate of formula (II) to obtain a metal complex having the structure of formula (IV):

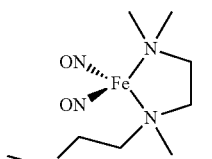
(III)

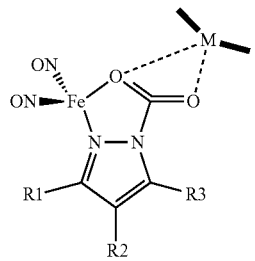
(IV)

In one embodiment, in step (i), $R_1$ is selected from a group consisting of hydrogen, methyl group, and benzyl group; each of $R_2$ and $R_3$ is independently hydrogen.

In one embodiment, in step (i), $M_1^{n+}$ is selected from a group consisting of $Na^+$, $K^+$, and $[K\text{-}18\text{-crown-}6\ ether]^+$.

In one embodiment in step (ii), the reaction of the pyrazole metal complex and carbon dioxide is carried out under an inert gas environment.

In one embodiment, the method further comprises a step (iv): providing a calcium trifluoromethanesulfonate ($Ca(OTf)_2$) for reacting with the metal complex of formula (IV) to obtain a calcium oxalate ($CaC_2O_4$).

In one embodiment, the method further comprises a step (v): providing a bis(pinacolato)diboron (($PinB)_2$) for reacting with the metal complex of formula (IV) to obtain a carbon monoxide.

In one embodiment, the method further comprises a step (vi): providing a 9-Borabicyclo(3.3.1)nonane (9-BBN) for reacting with the metal complex of formula (IV) to obtain a formic acid.

In one embodiment, the method further comprises a step (vii): providing a triethyl boride for reacting with the metal complex of formula (IV) to obtain a propionate.

In one embodiment, the method further comprises a step (viii): providing a zinc trifluoromethanesulfonate for reacting with the metal complex of formula (IV) to obtain a carbon dioxide reduction product.

DETAILED DESCRIPTION OF THE PREFERRED EMBODIMENT

Hereafter, examples will be provided to illustrate the embodiments of the present invention. The advantages and effects of the invention will become more apparent from the disclosure of the present invention. Other various aspects also may be practiced or applied in the invention, and various modifications and variations can be made without departing from the spirit of the invention based on various concepts and applications.

[Synthesis and Identification of the Pyrazole Metal Complex]

Firstly, reaction formula (a) is carried out by reacting sodium with pyrazole:

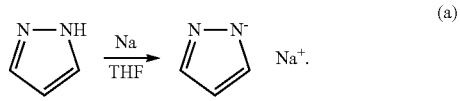

(a)

Figure 1:
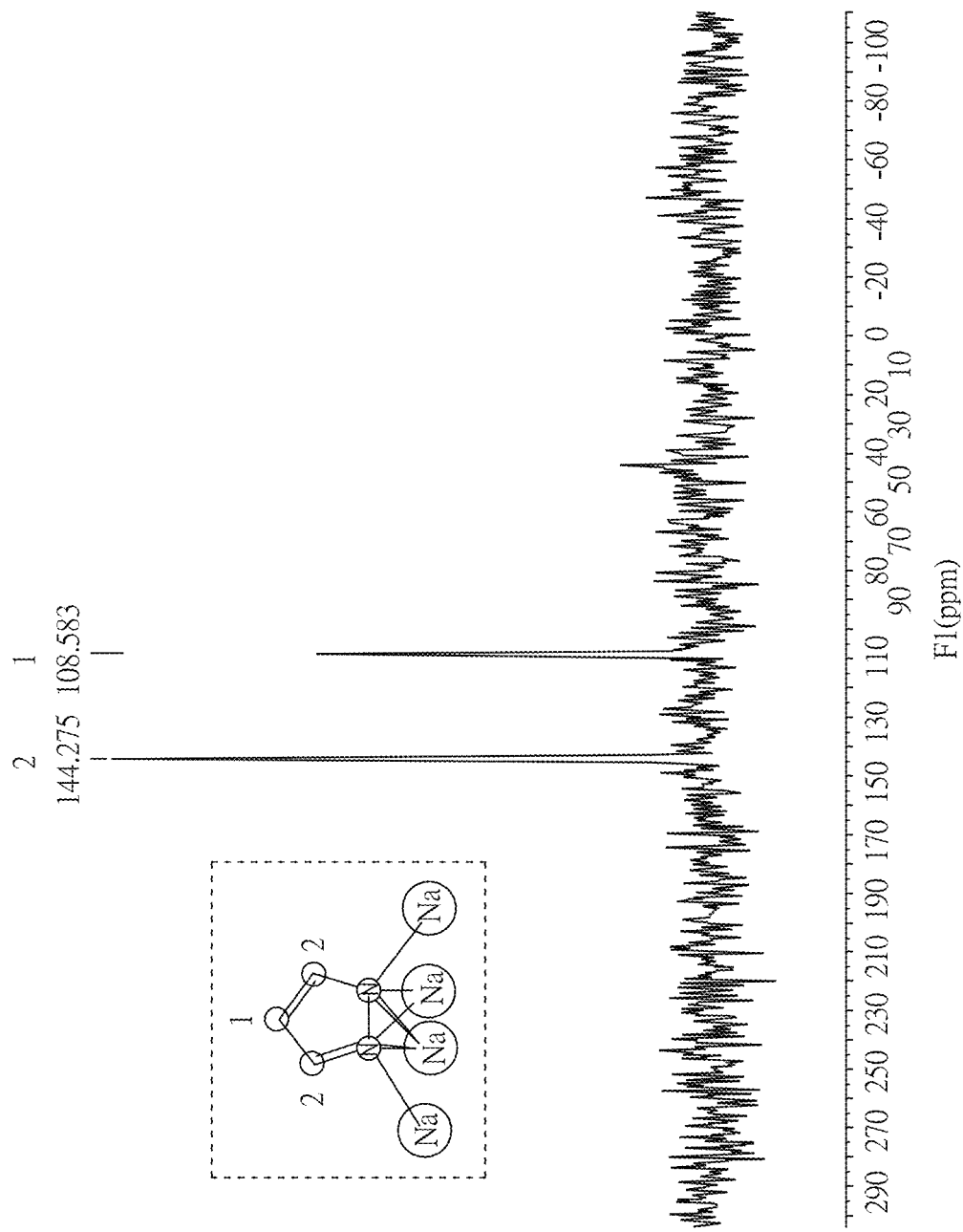
FIG. 1 is a $^{13}C$ solid NMR spectrum of Na-pyr of one embodiment of the present invention.
Figure 2:
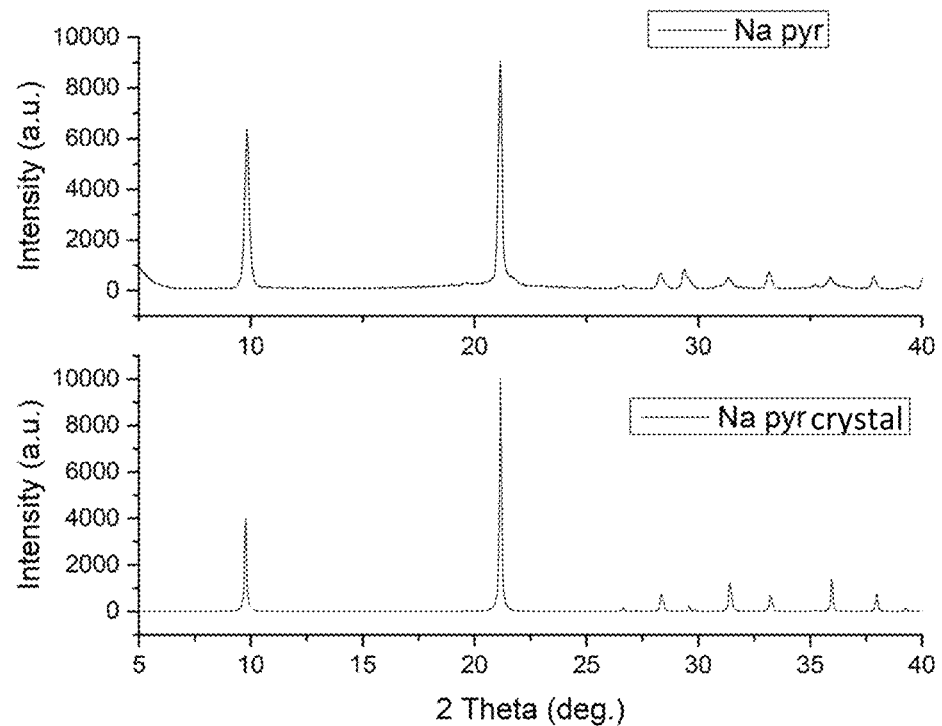
FIG. 2 is a powder X-ray diffraction pattern of Na-pyr and simulated spectrum of one embodiment of the present invention.

The product synthesized by the above reaction is identified as sodium pyrazolate (Na-pyr) according to the chemical shift (108.58/144.28 ppm) of the $^{13}$C solid NMR spectrum (FIG. 1), and comparison between the powder X-ray diffraction pattern of the product and simulated spectrum (FIG. 2).

Reaction formula (b) is carried out by reacting potassium hydride with pyrazole:

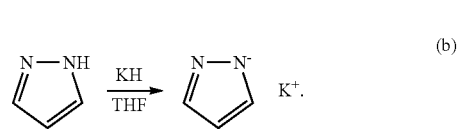

(b)

Figure 3:
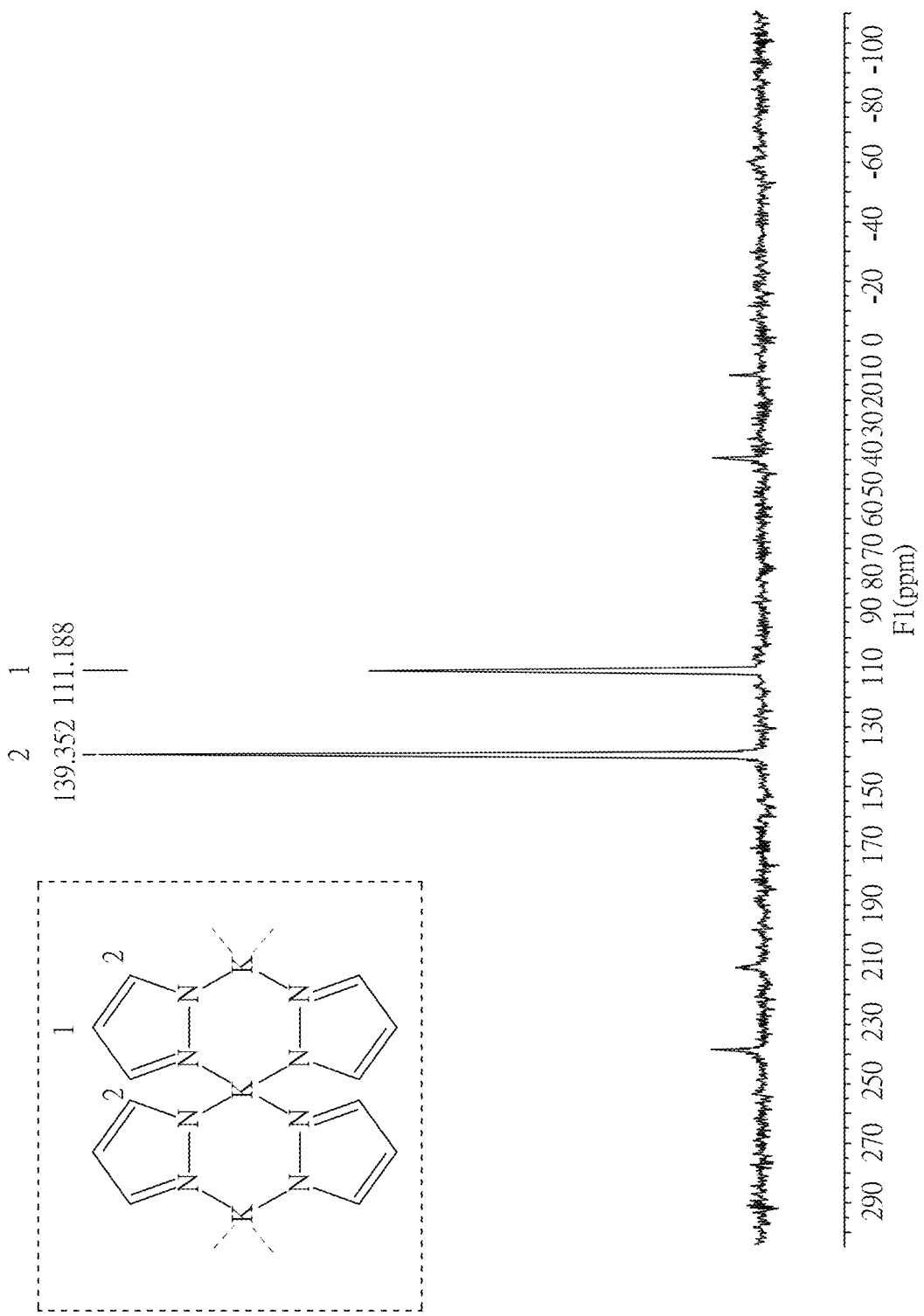
FIG. 3 is a $^{13}C$ solid NMR spectrum of K-pyr of one embodiment of the present invention.
Figure 4:
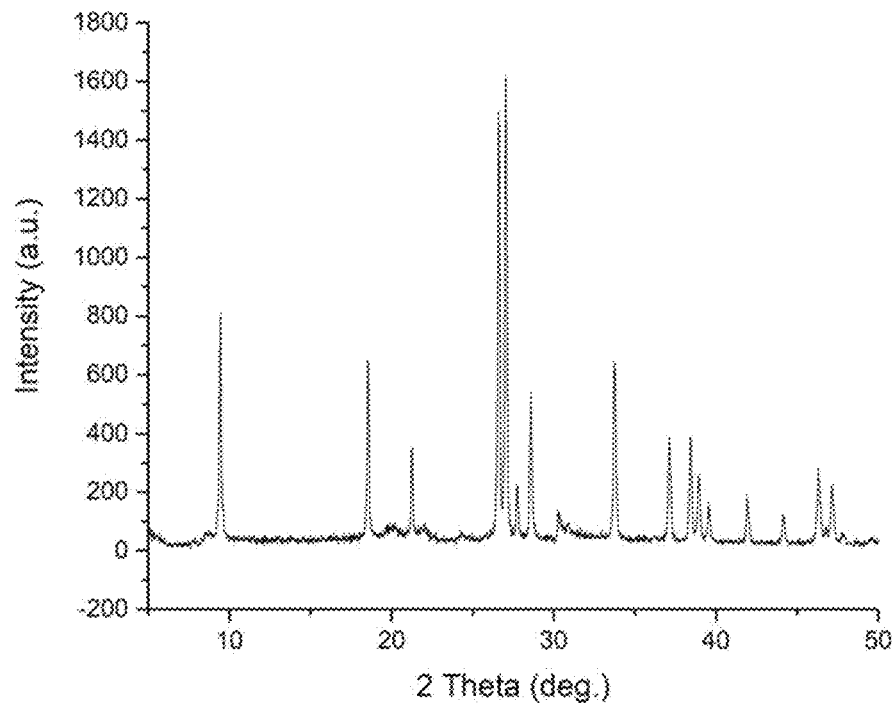
FIG. 4 is a powder X-ray diffraction pattern of K-pyr of one embodiment of the present invention.

The product synthesized by the above reaction is identified as potassium pyrazolate (K-pyr) according to the chemical shift (111.19/139.35 ppm) of the $^{13}$C solid NMR spectrum (FIG. 3), and the powder X-ray diffraction pattern of the product (FIG. 4) supports that the product has an orderly arrangement.

Further, reaction formula (C) is carried out by reacting potassium hydride and 18-crown-6 ether with pyrazole:

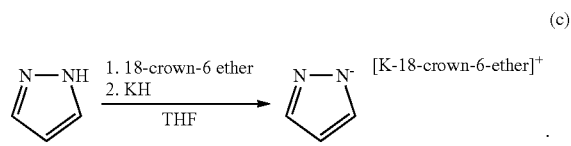

(c)

Figure 5:
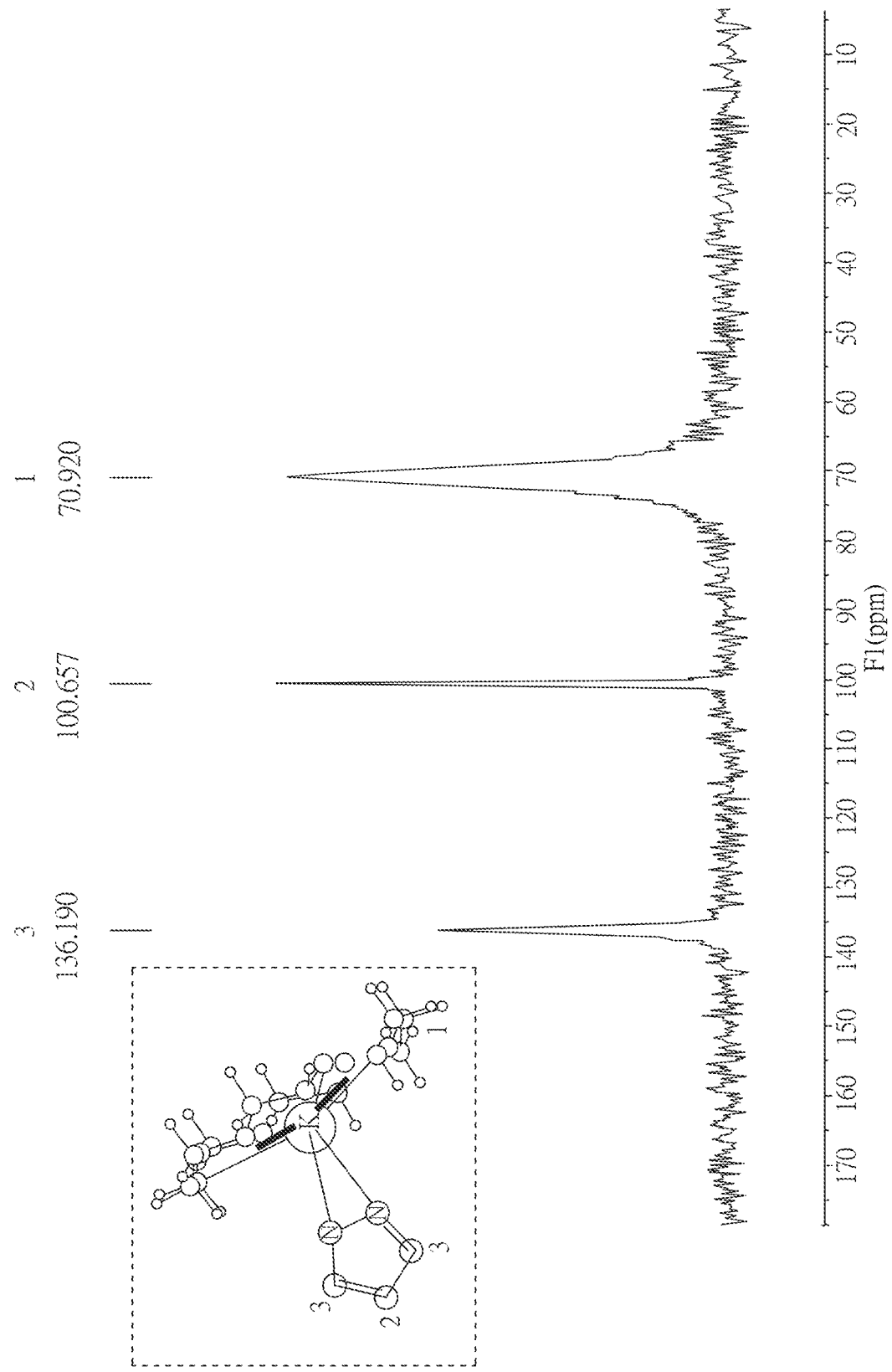
FIG. 5 is a $^{13}C$ solid NMR spectrum of 18-K-pyr of one embodiment of the present invention.
Figure 6:
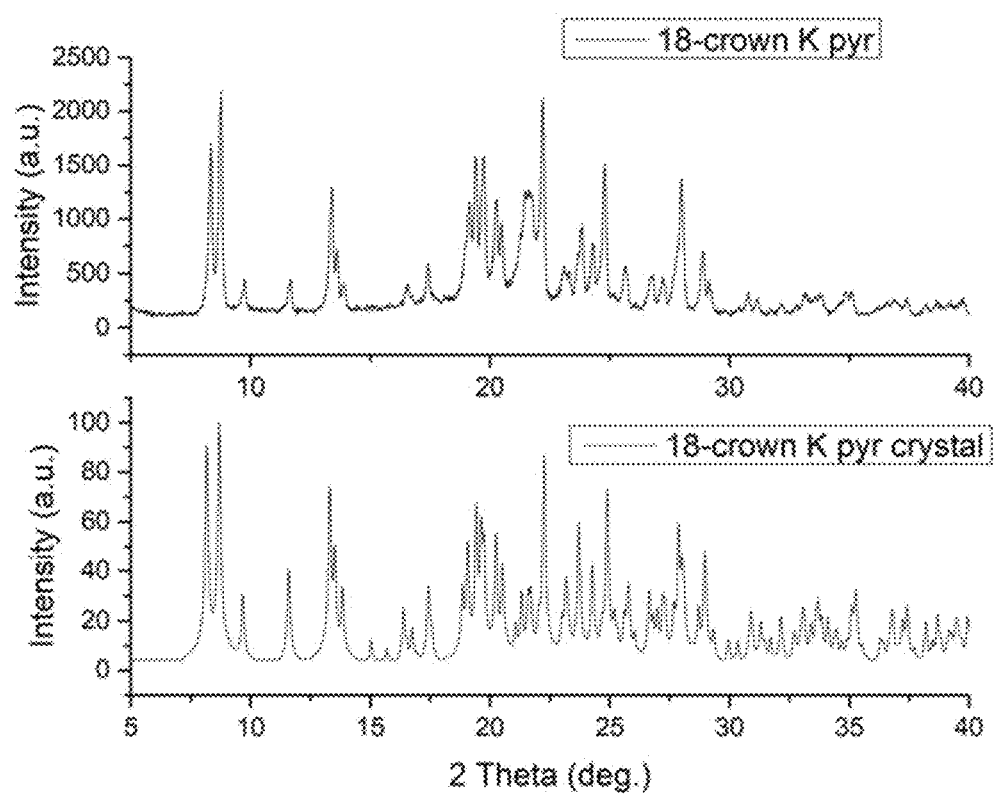
FIG. 6 is a powder X-ray diffraction pattern of 18-K-pyr and simulated spectrum of one embodiment of the present invention.

The product synthesized by the above reaction is identified as [K-18-crown-6-ether][pyr] (18-K-pyr) according to the chemical shift (70.92, 100.66, 136.190 ppm) of the $^{13}$C solid NMR spectrum (FIG. 5), and comparison between the powder X-ray diffraction pattern of the product and simulated spectrum (FIG. 6)

[Reaction of Pyrazole Metal Complex with Carbon Dioxide]

Firstly, reaction formula (d) is carried out by reacting Na-pyr with carbon dioxide:

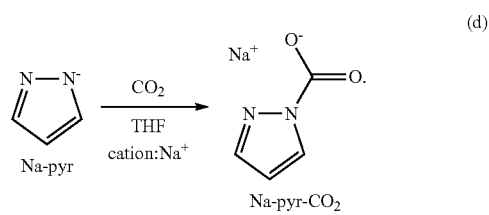

(d)

Figure 7:
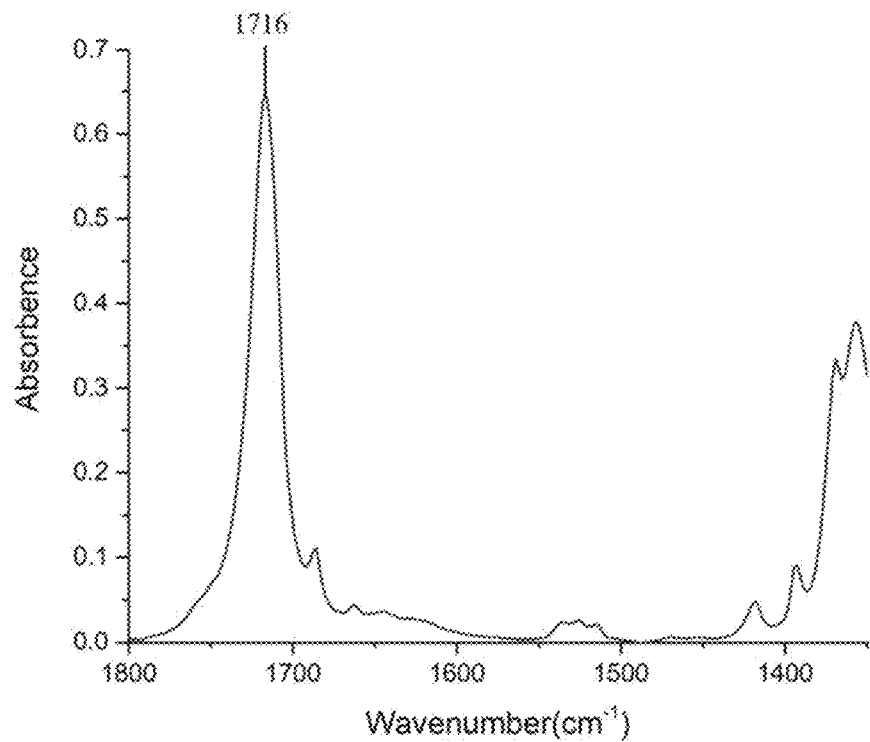
FIG. 7 is an IR vibration spectrum of Na-pyr-CO$_2$ of one embodiment of the present invention.
Figure 8:
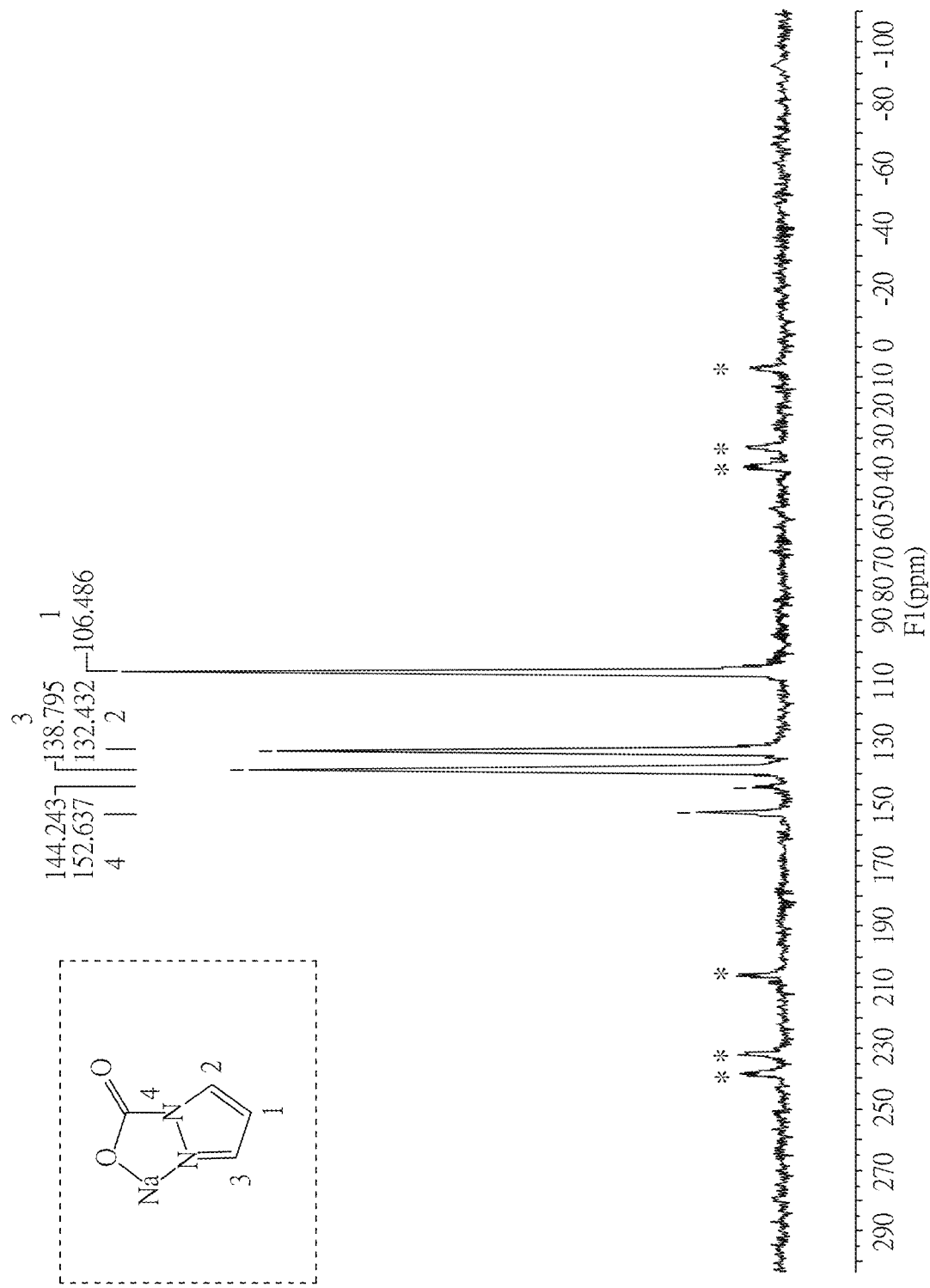
FIG. 8 is a $^{13}$C solid NMR spectrum of Na-pyr-CO$_2$ of one embodiment of the present invention.
Figure 9:
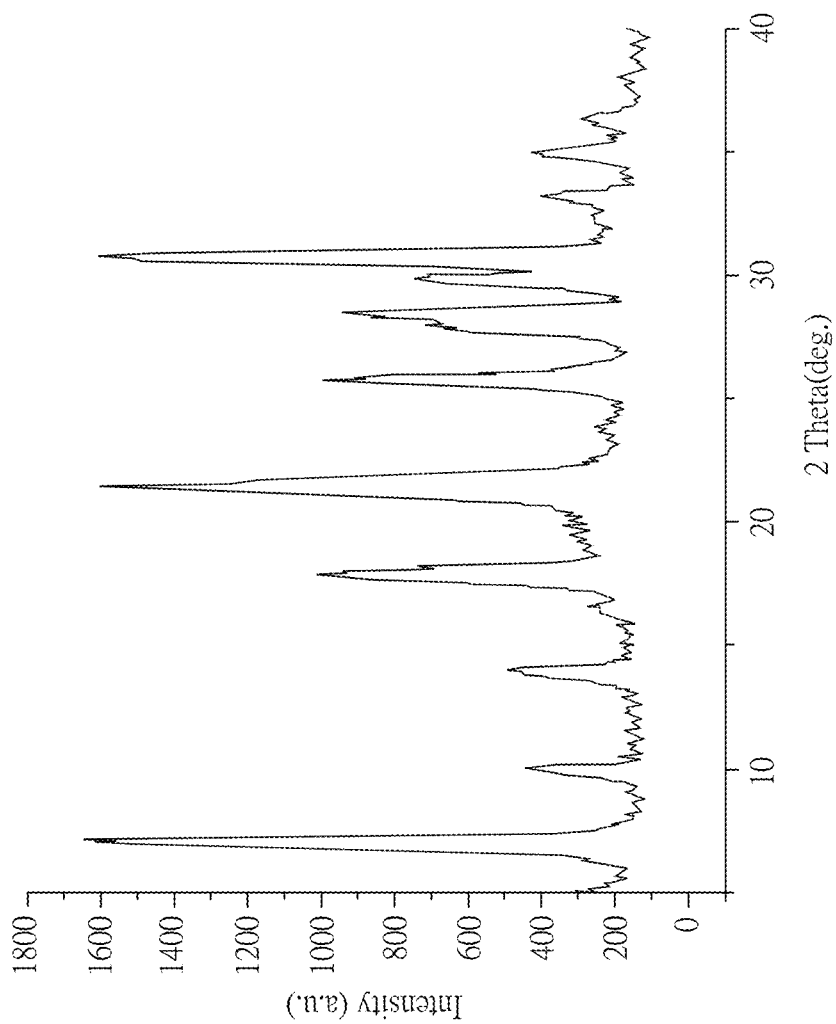
FIG. 9 is a powder X-ray diffraction pattern of Na-pyr-CO$_2$ of one embodiment of the present invention.

The reaction product Na-Pyr-CO$_2$ is identified according to the IR vibration spectrum (1716 cm$^{-1}$) (FIG. 7) and the chemical shift (152.64, 138.80, 132.43, and 106.5 ppm) of the $^{13}$C solid NMR spectrum (FIG. 8). Also, an orderly arrangement of the product is supported by the powder X-ray diffraction pattern (FIG. 9).

Reaction formula (e) is carried out by reacting K-pyr and carbon dioxide:

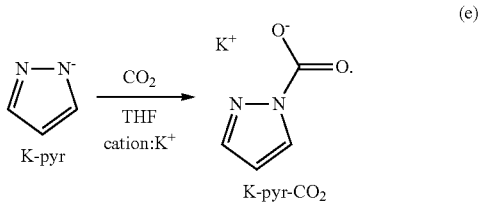

(e)

Figure 10:
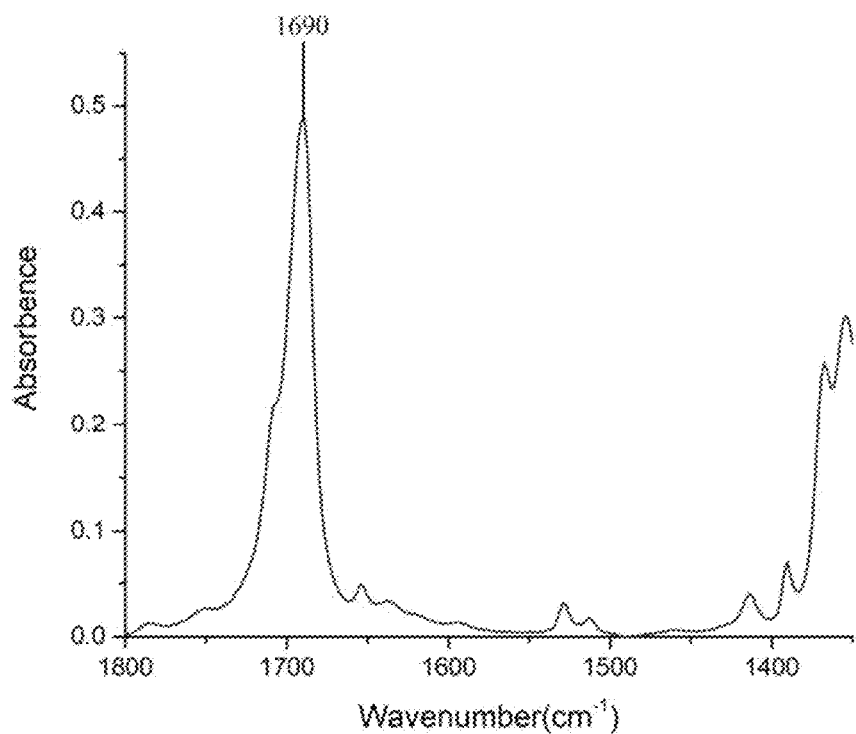
FIG. 10 is an IR vibration spectrum of K-pyr-CO$_2$ of one embodiment of the present invention.
Figure 11:
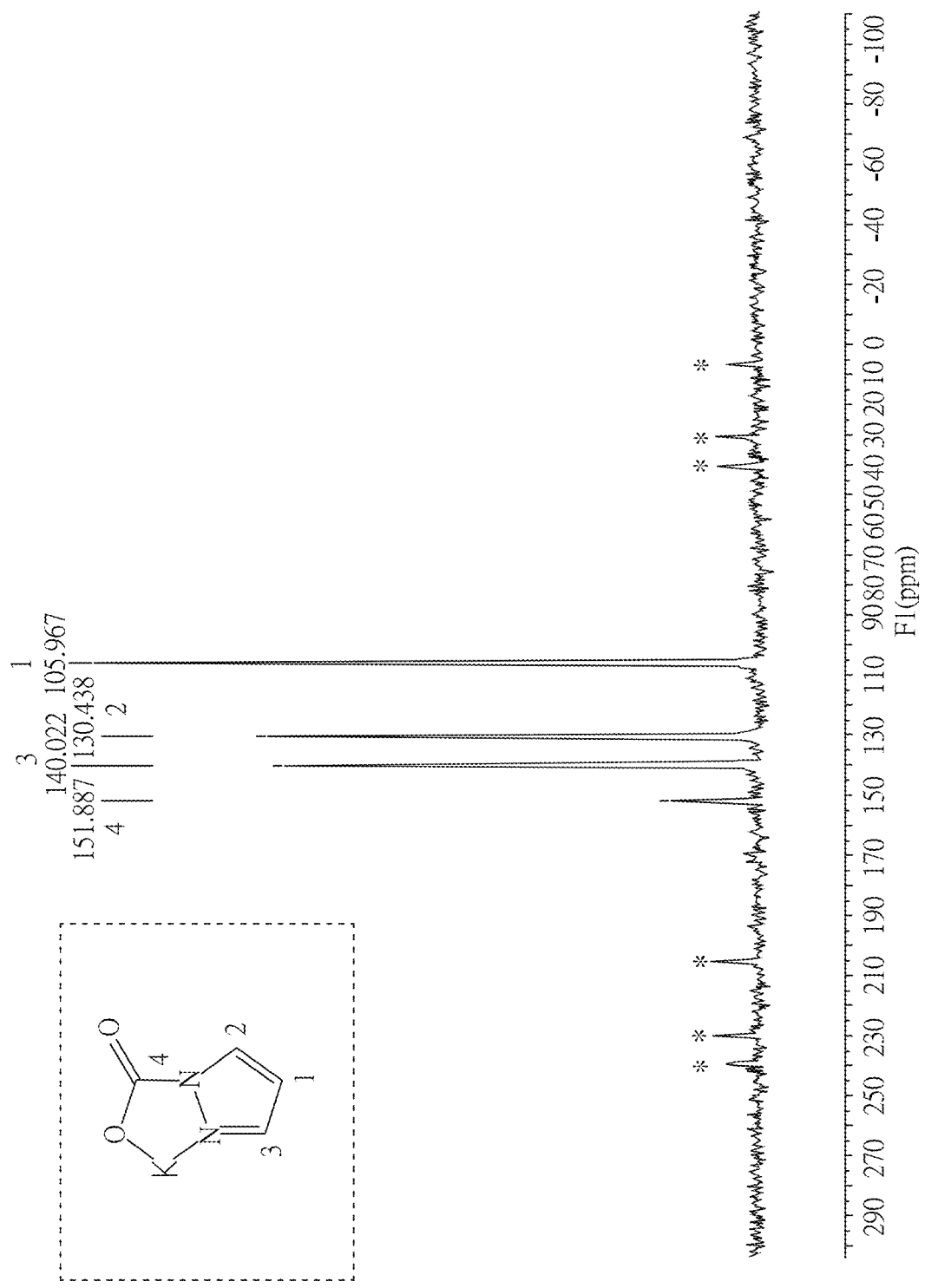
FIG. 11 is a $^{13}$C solid NMR spectrum of K-pyr-CO$_2$ of one embodiment of the present invention.
Figure 12:
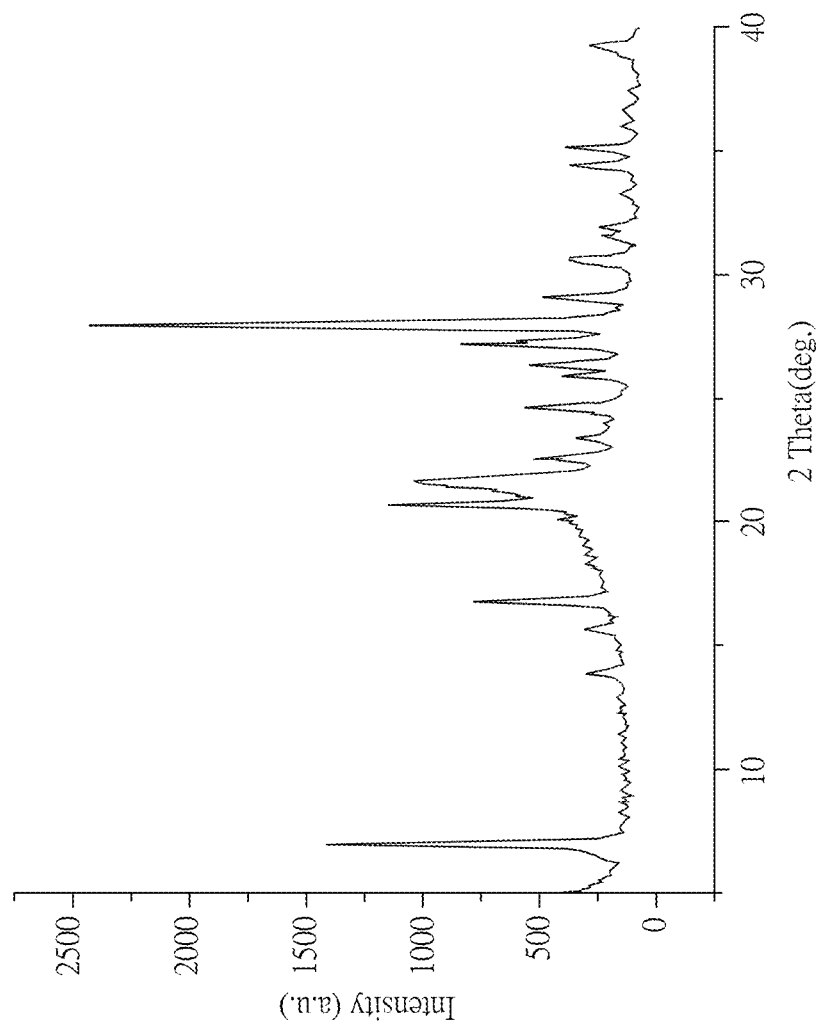
FIG. 12 is a powder X-ray diffraction pattern of K-pyr-CO$_2$ of one embodiment of the present invention.

The reaction product K-Pyr-CO$_2$ is identified according to the IR vibration spectrum (1690 cm-1) (FIG. 10) and the chemical shift (151.89, 140.02, 130.44, and 105.97 ppm) of the $^{13}$C solid NMR spectrum (FIG. 11). Also, an orderly arrangement of the product is supported by the powder X-ray diffraction pattern (FIG. 12).

[Pyrazole Metal Complex for the Capture of Carbon Dioxide]

Figure 13:
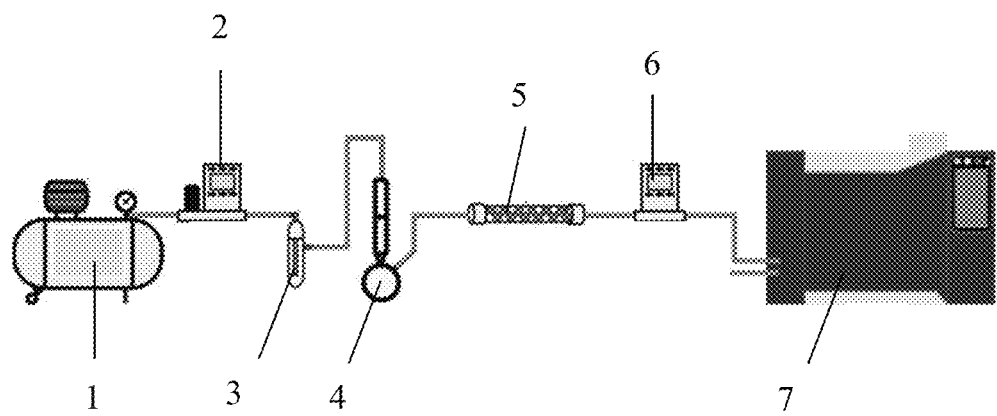
FIG. 13 is a schematic diagram of an air capture system of one embodiment of the present invention.

An air capture system 1000 illustrated in FIG. 13 is provided for testing the carbon dioxide capture ability of the pyrazole metal complex. The air capture system 1000 mainly includes an air compressor 1, a flow controller 2, a tubing 3, a sample column 4, a drying tube 5, a flow detector 6, and a gas chromatograph 7. The air output by the air compressor 1 is controlled at a flow rate of 200 mL/min by the flow controller 2 and passes through the tubing 3 contained with water so that the air is humidified. Next, the air passes through the sample column 4 filled with different pyrazole metal complexes whilst the pyrazole metal complex in the sample column captures the carbon dioxide in the air. After carbon dioxide is captured from the air by different pyrazole metal complexes and water is removed from the air by the drying tube 5, the air flows into the gas chromatograph 7 for detection of the concentration of carbon dioxide.

Figure 14:
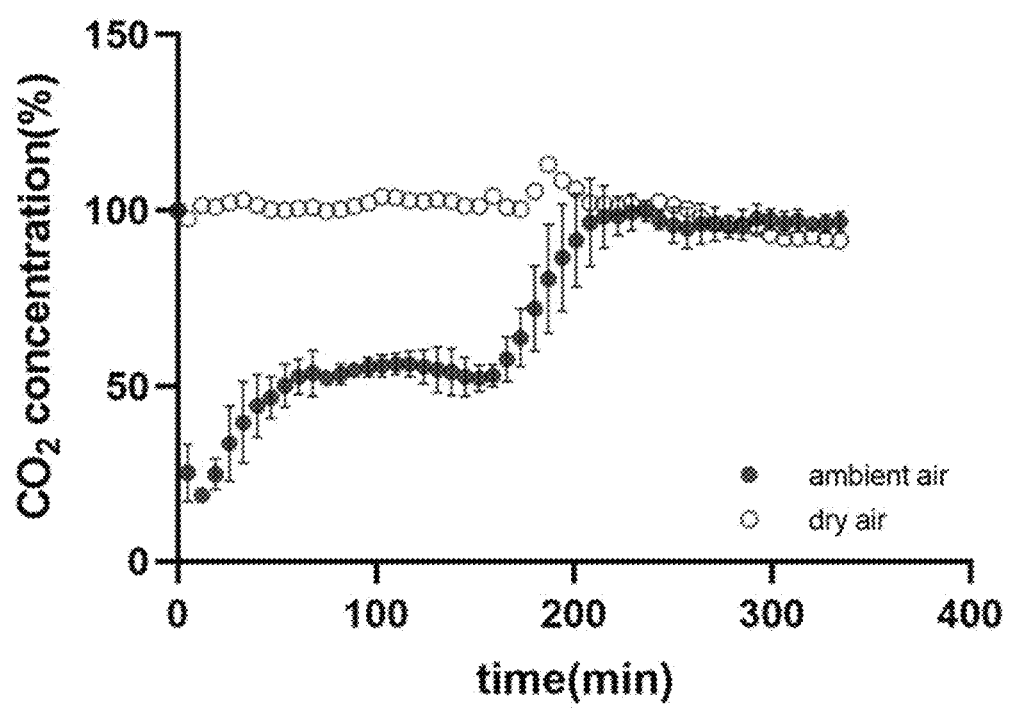
FIG. 14 is a schematic diagram of the detection results of the air capture system of one embodiment of the present invention.

First, the above-mentioned air capture procedure is performed with the sample column 4 filled with Na-pyr. Dry air and humidified air are independently provided and the detection results are shown in FIG. 14. According to the results shown in FIG. 14, Na-pyr can capture 80 percent of the carbon dioxide for 20 minutes and capture 50 percent of the carbon dioxide for 160 minutes whilst the air is humidified. However, the ability to capture carbon of the pyrazole metal complexes in dry air dioxide is poor.

Figure 15:
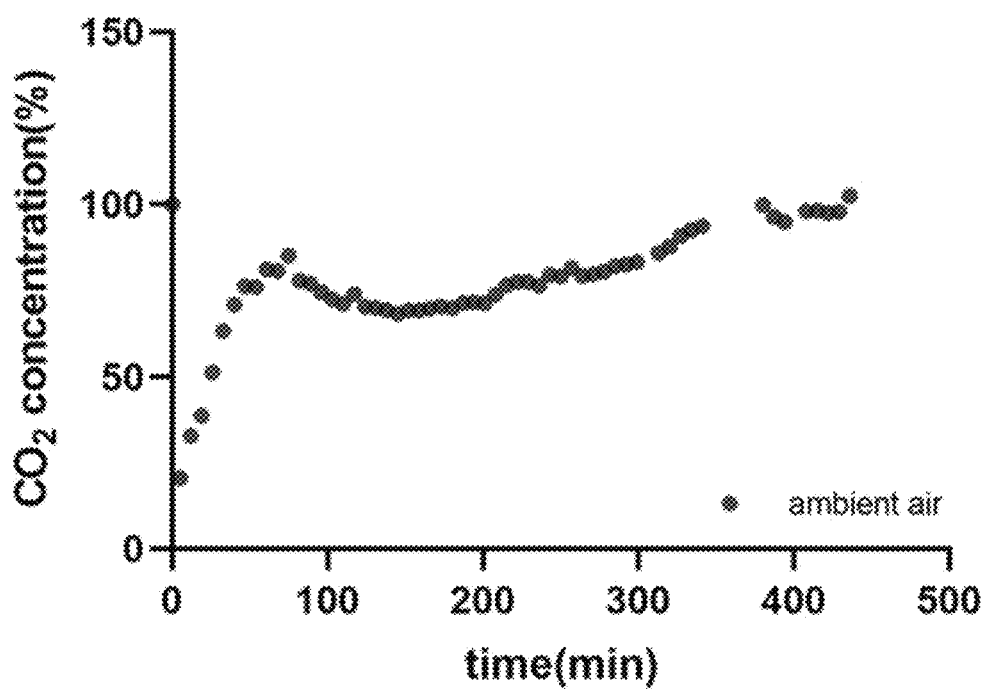
FIG. 15 is a schematic diagram of the detection results of the air capture system of one embodiment of the present invention.

Next, the air capture procedure is performed with the sample column 4 filled with Na-3-methylpyrazolate (Na-3-mpyr) with a methyl substituent at position 3. Humidified air is provided and the detection result is shown in FIG. 15. According to the result shown in FIG. 15, Na-3-mpyr has the ability to capture carbon dioxide from the humidified air.

Figure 16:
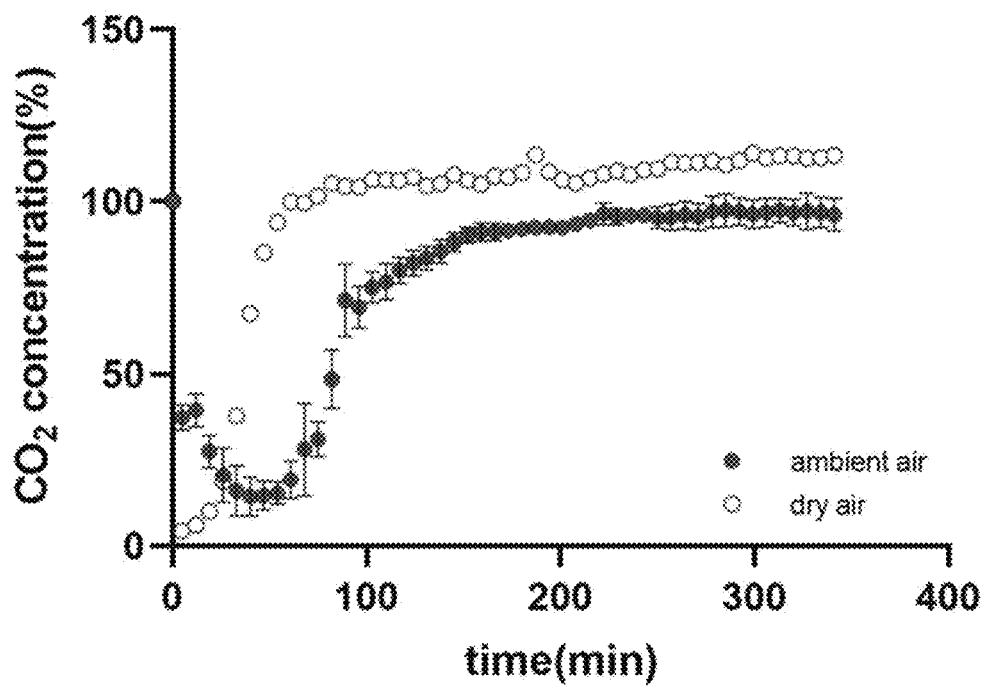
FIG. 16 is a schematic diagram of the detection results of the air capture system of one embodiment of the present invention.

Furthermore, the air capture procedure is performed with the sample column 4 filled with K-pyr. Dry air and humidified air are provided and the detection result is shown in FIG. 16. According to the result shown in FIG. 16, K-pyr can capture 20 percent of the carbon dioxide for 60 minutes from the humidified air; K-pyr also has the ability to capture carbon dioxide in dry air.

Figure 17:
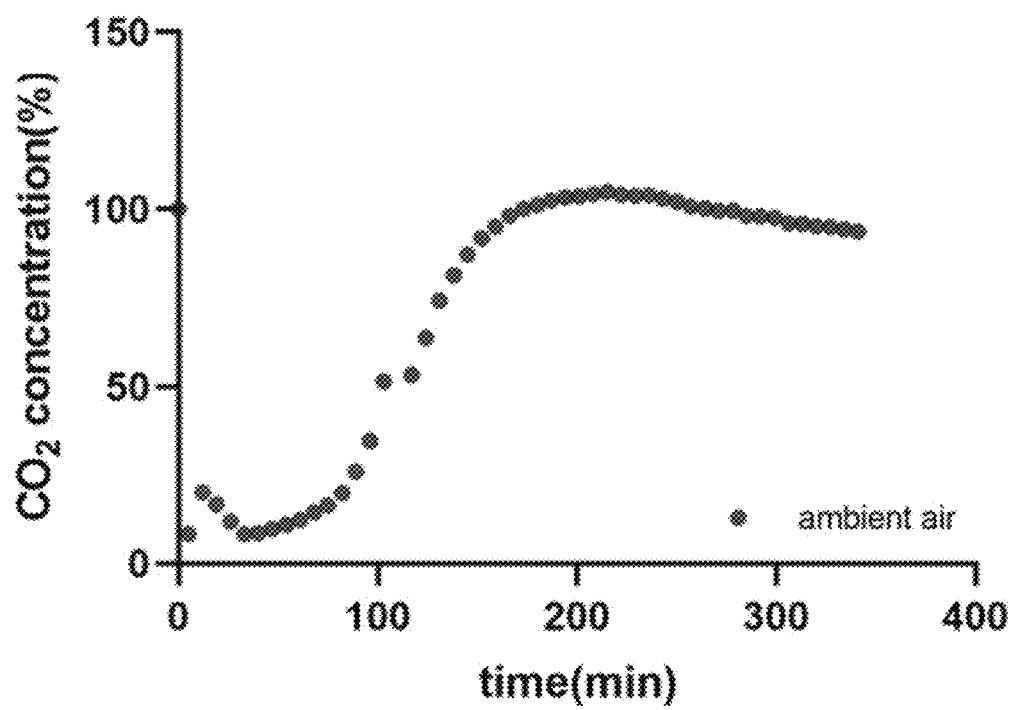
FIG. 17 is a schematic diagram of the detection results of the air capture system of one embodiment of the present invention.

Next, the air capture procedure is performed with the sample column 4 filled with K-3-methylpyrazolate (K-3-mpyr) with a methyl substituent at position 3. Humidified air is provided and the detection result is shown in FIG. 17. According to the result shown in FIG. 17, K-3-mpyr has the ability to capture carbon dioxide from the humidified air.

Figure 18:
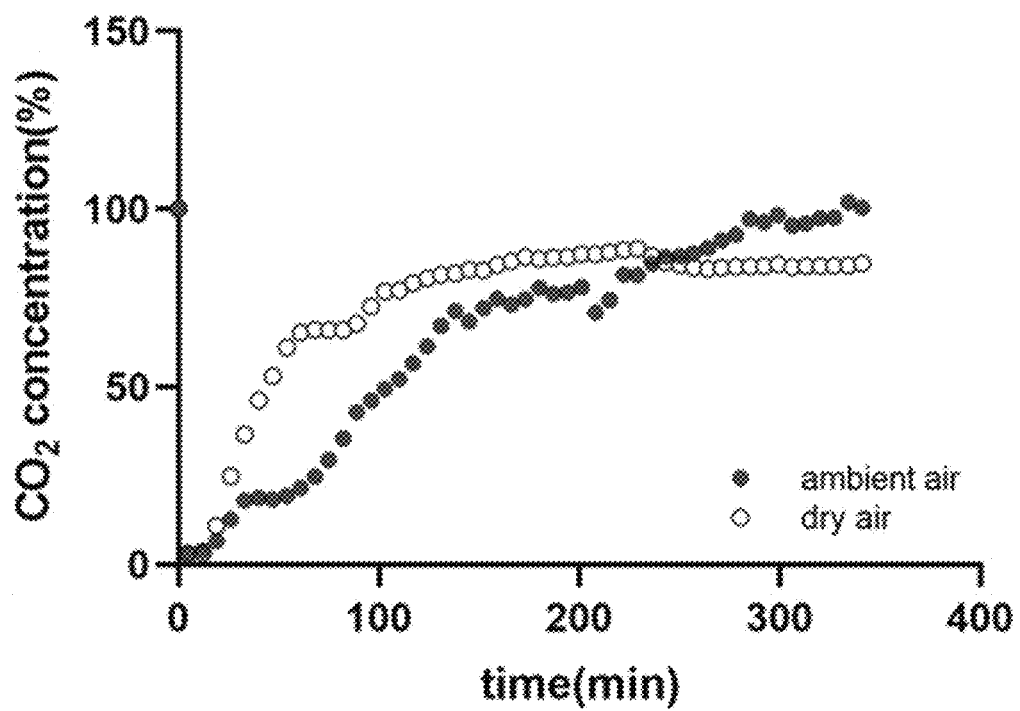
FIG. 18 is a schematic diagram of the detection results of the air capture system of one embodiment of the present invention.

Furthermore, the air capture procedure is performed with the sample column 4 filled with 18-K-pyr. Dry air and humidified air are provided and the detection result is shown in FIG. 18. According to the result shown in FIG. 18, 18-K-pyr can capture over 95 percent of the carbon dioxide for 20 minutes from the humidified air and the dry air.

According to the test results, each of pyrazole metal complexes including Na-pyr, Na-3-mpyr, K-pyr, K-3-mpyr, and 18-K-pyr has the ability to capture carbon dioxide in the air.

The product obtained after capturing carbon dioxide by the pyrazole metal complex can be further combined with different chemical reagents to reduce carbon dioxide into economically valuable products.

[Conversion of Carbon Dioxide to Calcium Oxalate]

The product of Na-3-mpyr or K-3-mpyr capturing carbon dioxide is shown in formula (II-1):

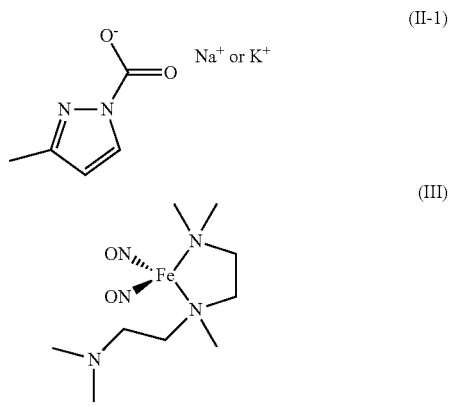

Next, reacting the product (II-1) with the double nitroso iron complex of formula (III) to obtain a metal complex of formula (IV-1):

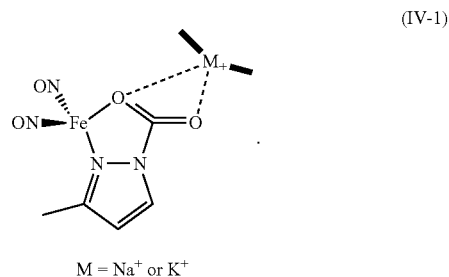

Figure 19:
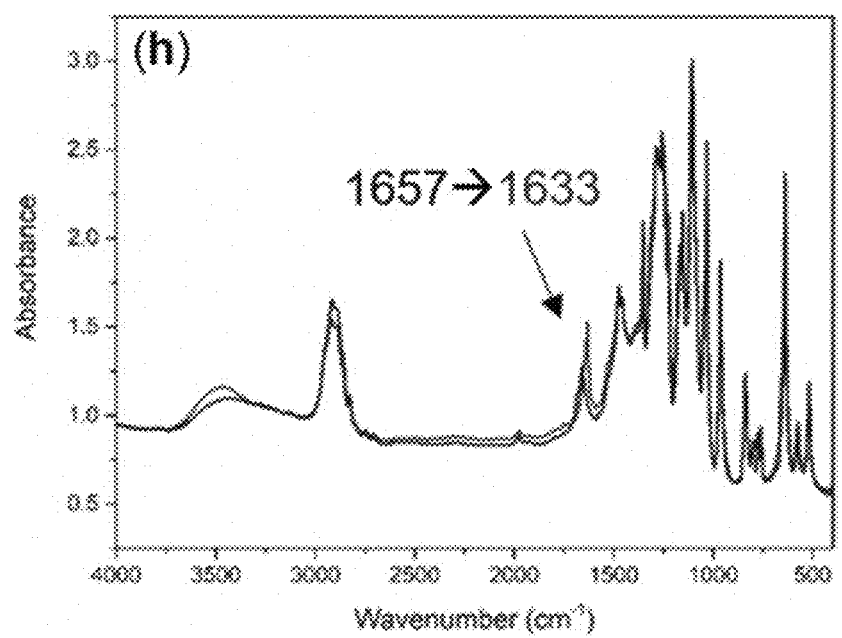
FIG. 19 is an IR vibration spectrum of the product of one embodiment of the present invention.
Figure 20:
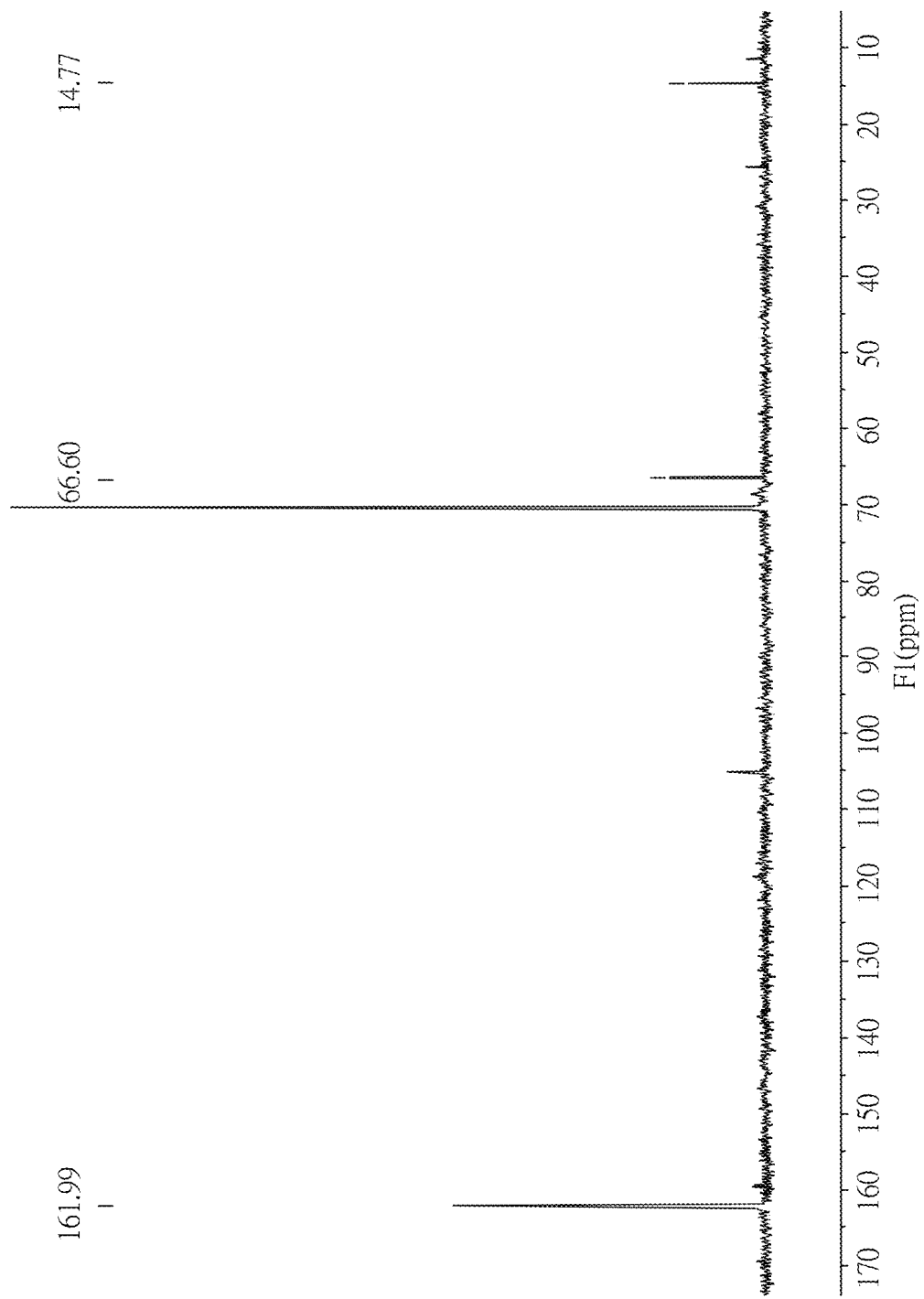
FIG. 20 is a $^{13}$C solid NMR spectrum of the product of one embodiment of the present invention.

Furthermore, reacting the metal complex 2CO$_2$ of formula (IV-1) with the calcium trifluoromethanesulfonate (Ca(OTf)$_2$), the product is characterized by the IR absorption peak at 1657 cm$^{-1}$ (FIG. 19). The absorption peak of the product obtained by reacting 2-$^{13}$CO$_2$ is shifted to 1633 cm$^{-1}$ (FIG. 19). According to the IR vibration spectrum, the formation of the carbon dioxide reduction product is confirmed. In addition, the carbon dioxide reduction product is also confirmed by the chemical shift 161.99 ppm in the NMR spectrum (FIG. 20).

[Conversion of Carbon Dioxide to Carbon Monoxide]

Figure 21:
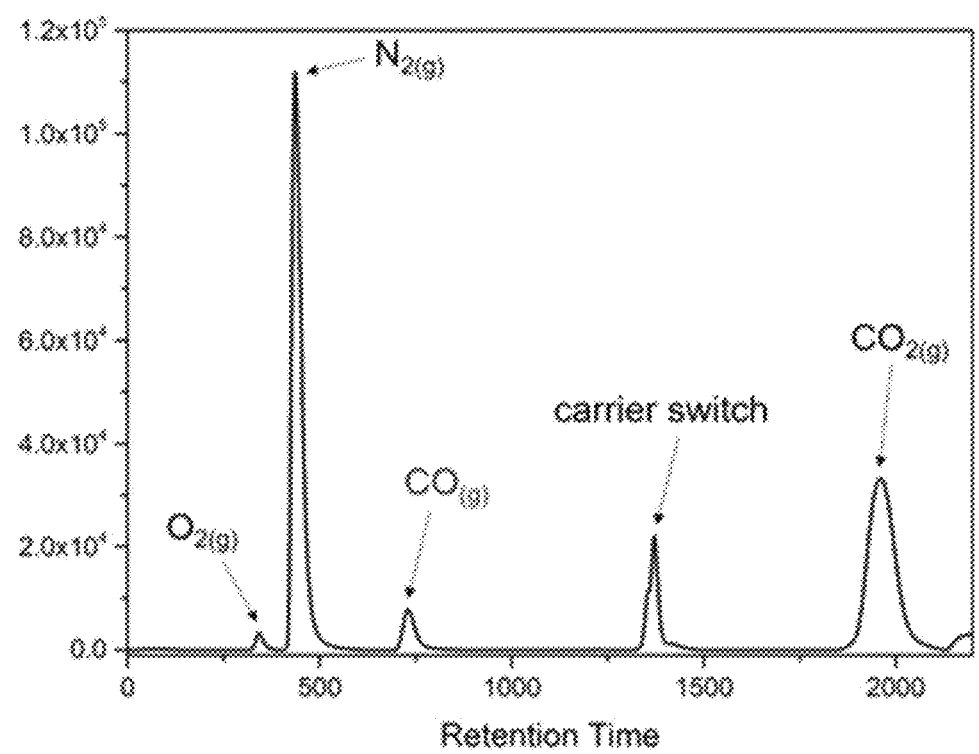
FIG. 21 is a GC chromatogram of the product of one embodiment of the present invention.

Similarly, reacting the product (II-1) of Na-3-mpyr or K-3-mpyr capturing carbon dioxide with the double nitroso iron complex of formula (III) to obtain a metal complex of formula (IV-1). Then, reacting the metal complex 2-CO$_2$ and bis(pinacolato)diboron, the air after the reaction is collected and is confirmed by the gas chromatograph that the reaction converts carbon dioxide into carbon monoxide (FIG. 21).

[Conversion of Carbon Dioxide to Formic Acid]

Figure 22:
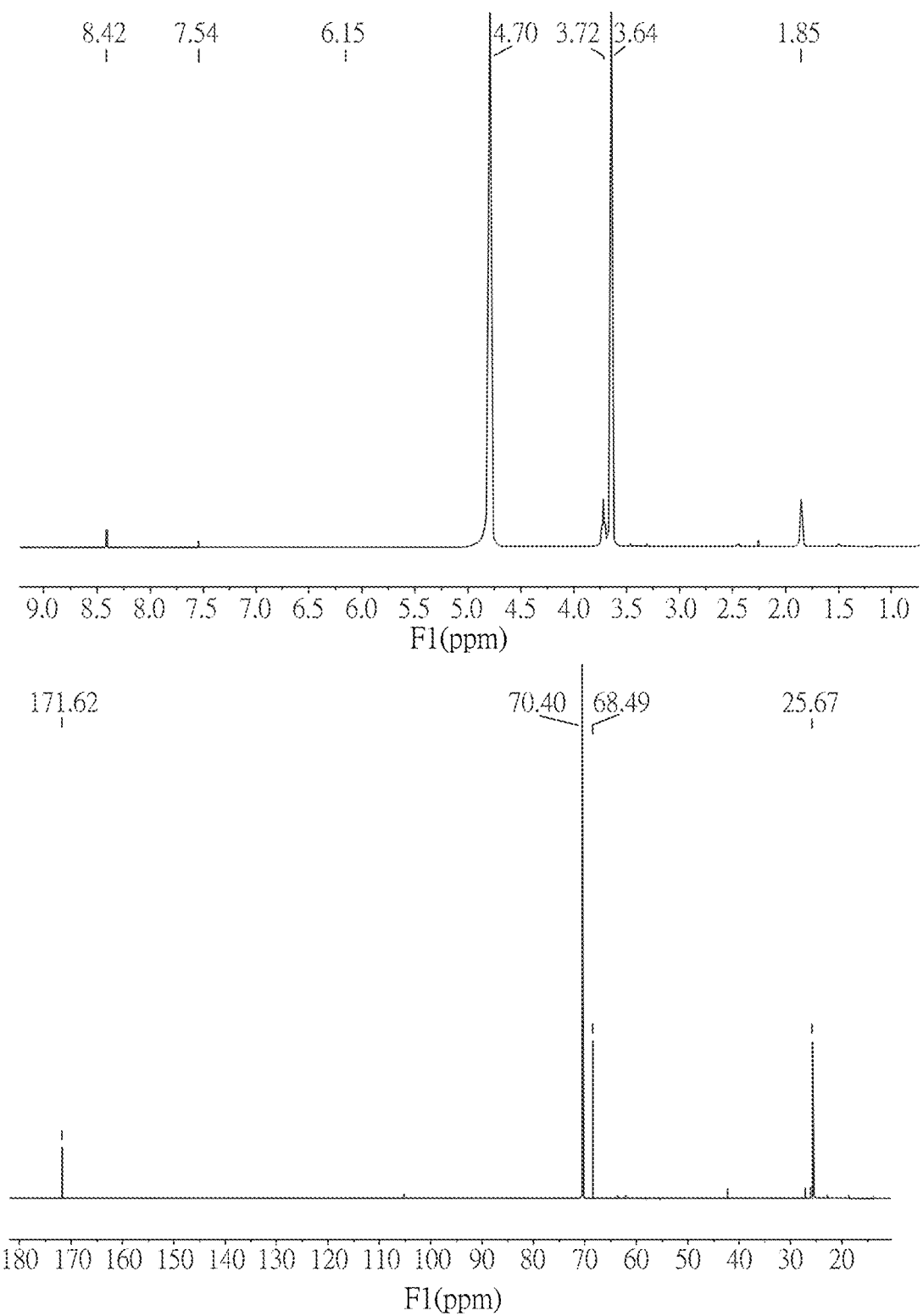
FIG. 22 shows a $^1$H NMR spectrum and a $^{13}$C NMR spectrum of the product of one embodiment of the present invention.

Similarly, the product collected by reacting the metal complex 2-CO$_2$ represented by formula (IV-1) with 9-borabicyclo(3.3.1)nonane is dissolved in heavy water. It is confirmed that the reaction converts carbon dioxide into formate by the chemical shift 8.42 ppm in $^1$H NMR spectrum and 171.62 ppm in $^{13}$C NMR spectrum (FIG. 22).

[Conversion of Carbon Dioxide to Propionate]

Similarly, reacting the product (II-1) of Na-3-mpyr or K-3-mpyr capturing carbon dioxide with the double nitroso iron complex of formula (III) to obtain a metal complex of formula (IV-1).

Figure 23:
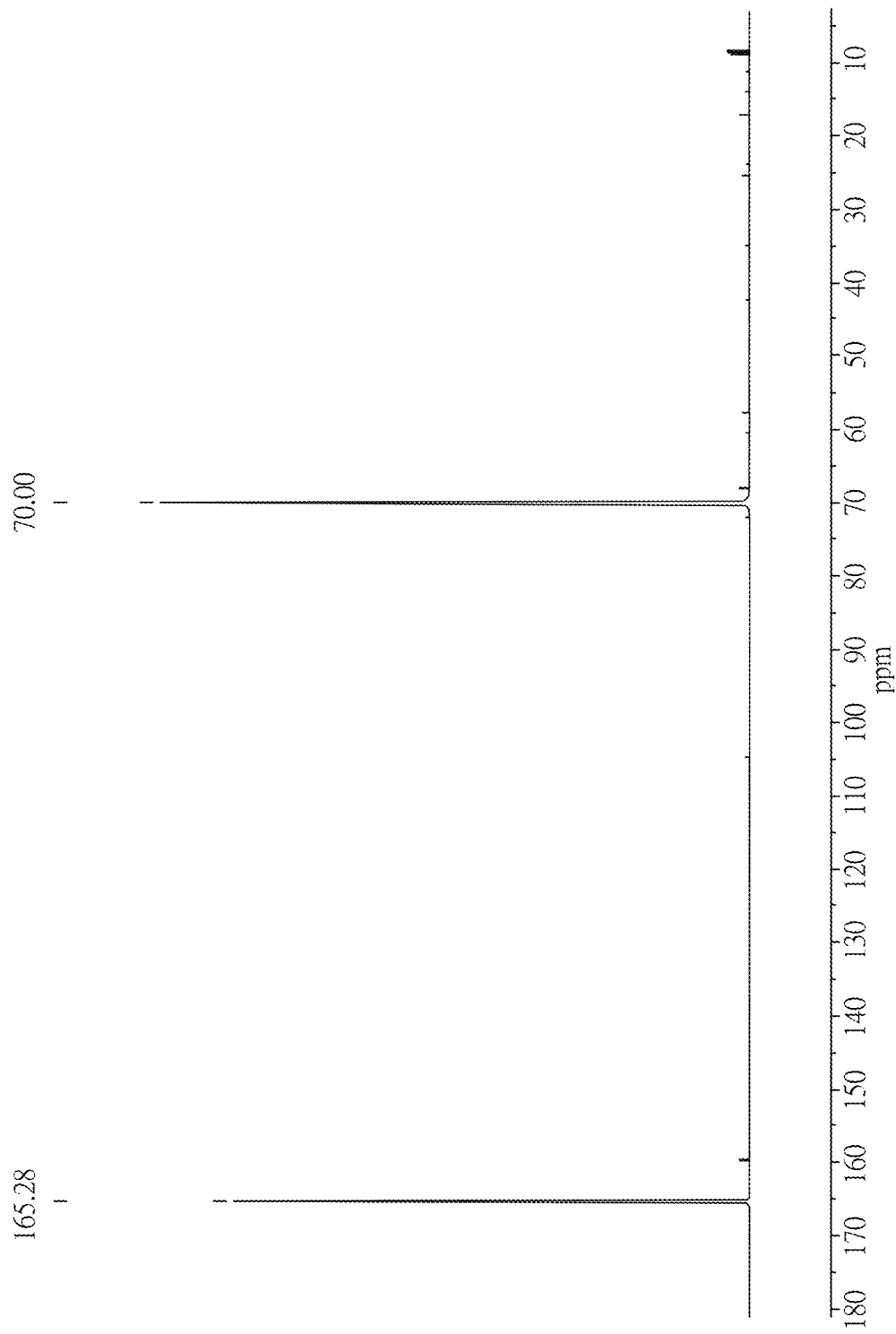
FIG. 23 is a $^{13}$C NMR spectrum of the product of one embodiment of the present invention.

The product of reacting the metal complex 2-$^{13}$CO$_2$ with triethyl boride is dissolved in heavy water. It is confirmed that the reaction converts carbon dioxide into propionate by the chemical shift 165.28 ppm in $^{13}$C NMR spectrum (FIG. 23).

[Capture and Purification of Carbon Dioxide]

Figure 24:
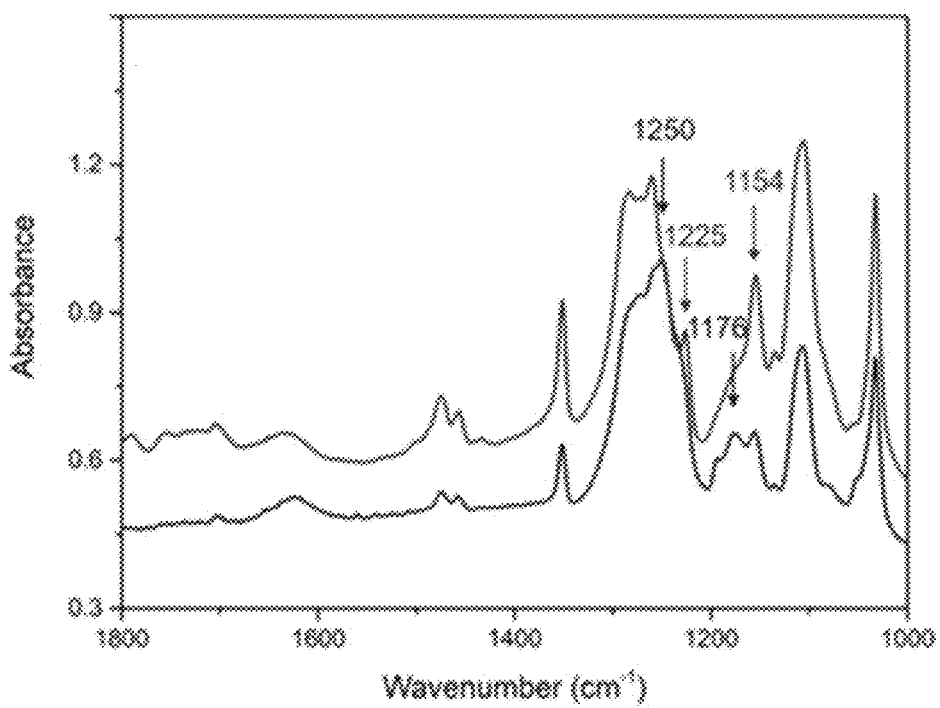
FIG. 24 is an IR vibration spectrum of the product of one embodiment of the present invention.
Figure 25:
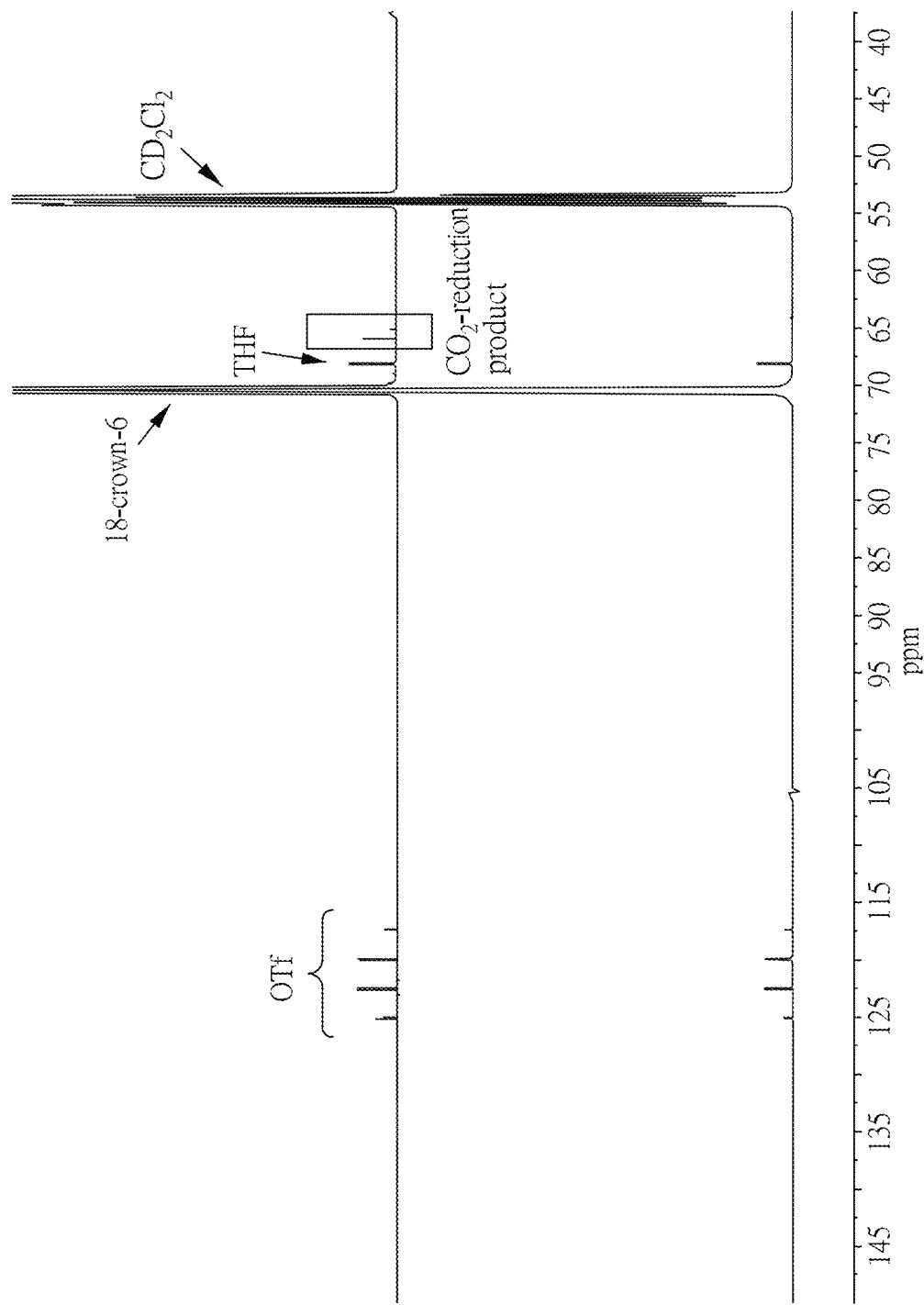
FIG. 25 is a $^{13}$C NMR spectrum of the product of one embodiment of the present invention.

The product obtained by reacting metal complex 2-CO$_2$ represent by formula (IV-1) with zinc trifluoromethanesulfonate is characterized by the IR absorption peaks at 1250 cm$^{-1}$ and 1176 cm$^{-1}$ (FIG. 24). When 2-$^{13}$CO$_2$ is used, the IR absorption peaks shift to 1225 cm$^{-1}$ and 1154 cm$^{-1}$ (FIG. 24). According to the IR vibration spectrum, the formation of the carbon dioxide reduction product is confirmed. Also, it is confirmed that the reaction converts carbon dioxide into a carbon dioxide reduction product by the chemical shift 66.4 ppm and 65.6 ppm in $^{13}$C NMR spectrum (FIG. 25) when 2-$^{13}$CO$_2$ is used.

[Reduction of the Pyrazole Metal Complex]

After the pyrazole metal complex captures carbon dioxide, reacts with the double nitroso iron complex represented by formula (III), and further reacts with calcium triflate to form calcium oxalate, the side product obtained can further react with protonated pentamethyldiethylenetriamine (PMDTA) to form a pyrazole compound and the double nitroso iron complex represented by formula (III), wherein the pyrazole can further convert into the pyrazole metal complex of the present invention. That is, the pyrazole metal complex of the present invention and the double nitroso iron complex can be recovered after the capture of CO$_2$ and forming calcium oxalate.

In summary, the pyrazole metal complex of the present invention is capable of capturing carbon dioxide efficiently, the product yields after capturing carbon dioxide can be converted to several economically valuable compounds such as carbon monoxide, calcium oxalate, formate, and propionate, or can be converted to carbon dioxide reduction product through reactions. Also, the pyrazole metal complex and the double nitroso iron complex required in the reaction can further be recovered and reused, which meets the requirements of low cost and environmental friendly.

What is claimed is:

1. A method for absorbing carbon dioxide, comprising:

step (i): providing a pyrazole metal complex of formula (I)

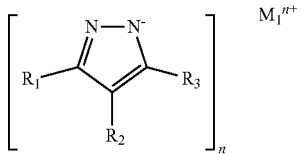

wherein R$_1$ is selected from the group consisting of hydrogen, methyl group, and benzyl group; each of R$_2$ and R$_3$ is independently hydrogen; and M$_1^{n+}$ is selected from the group consisting of Na$^+$, K$^+$, and [K-18-crown-6 ether]$^+$; and step (ii): reacting the pyrazole metal complex with carbon dioxide for absorbing carbon dioxide, wherein a product obtained by reacting the pyrazole metal complex and carbon dioxide is a pyrazole amide formate of formula (II):

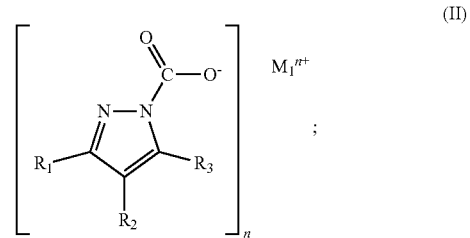

and step (iii): providing a double nitroso iron complex of formula (III) for reacting with the pyrazole amide formate of formula (II) to obtain a metal complex having structure of formula (IV):

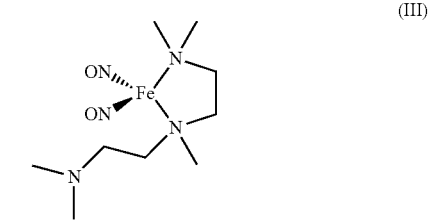

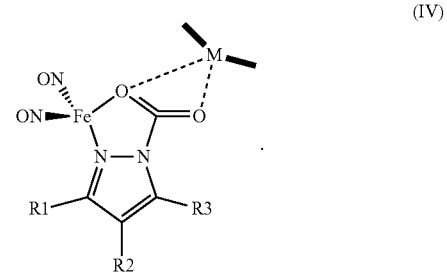

wherein M is Na$^+$ or K$^+$.

2. The method of claim 1, wherein step (i), M$_1^{n+}$ is selected from the group consisting of Na$^+$, K$^+$, and [K-18-crown-6 ether]$^+$.

3. The method of claim 1, wherein step (ii), the reaction of the pyrazole metal complex and carbon dioxide is carried out under an inert gas environment.

4. The method of claim 1, further comprising:

step (iv): providing a calcium trifluoromethanesulfonate (Ca(OTf)$_2$) for reacting with the metal complex of formula (IV) to obtain a calcium oxalate (CaC$_2$O$_4$).

5. The method of claim 1, further comprising:

step (v): providing a bis(pinacolato) diboron ((PinB)$_2$) for reacting with the metal complex of formula (IV) to obtain a carbon monoxide.

6. The method of claim 1, further comprising:
step (vi): providing a 9-Borabicyclo(3.3.1)nonane (9-BBN) for reacting with the metal complex of formula (IV) to obtain a formic acid.
7. The method of claim 1, further comprising:
step (vii): providing a triethyl boride for reacting with the metal complex of formula (IV) to obtain a propionate.
8. The method of claim 1, further comprising:
step (viii): providing a zinc trifluoromethanesulfonate for reacting with the metal complex of formula (IV) to obtain a carbon dioxide reduction product.

\* \* \* \* \*